US009125848B2

(12) United States Patent
Tuohy et al.

(10) Patent No.: US 9,125,848 B2
(45) Date of Patent: Sep. 8, 2015

(54) ALPHA LACTALBUMIN IMMUNIZATION METHODS

(75) Inventors: Vincent K. Tuohy, Broadview Heights, OH (US); Justin M. Johnson, Willoughby Hills, OH (US); Ritika Jaini, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 269 days.

(21) Appl. No.: 13/157,990

(22) Filed: Jun. 10, 2011

(65) Prior Publication Data

US 2012/0003254 A1 Jan. 5, 2012

Related U.S. Application Data

(60) Provisional application No. 61/353,825, filed on Jun. 11, 2010, provisional application No. 61/353,464, filed on Jun. 10, 2010, provisional application No. 61/353,470, filed on Jun. 10, 2010.

(51) Int. Cl.
 *A61K 39/00* (2006.01)
 *A61P 35/00* (2006.01)
 *A61K 38/16* (2006.01)

(52) U.S. Cl.
 CPC ....... *A61K 39/0011* (2013.01); *A61K 2039/572* (2013.01)

(58) Field of Classification Search
 None
 See application file for complete search history.

(56) References Cited

U.S. PATENT DOCUMENTS

| 6,812,339 B1 | 11/2004 | Venter et al. |
| 2007/0099833 A1 | 5/2007 | Rosen et al. |

FOREIGN PATENT DOCUMENTS

WO   WO 2008058547 A2  *  5/2008

OTHER PUBLICATIONS

Sawyers et al. The cancer biomarker problem. Nature. 452(7187):548-52, Apr. 3, 2008.*
Hall et al. alpha-Lactalbumin is not a marker of human hormone-dependent breast cancer. Nature. 290:602-604, 1981.*
Walker et al. The demonstration of alpha lactalbumin in human breast carcinomas. The Journal of Pathology. 129(1):37-42, 1979.*
Richmond et al. Mouse xenograft models vs GEM models for human cacner therapeutics. Disease Models and Mechanisms. 1(2-3):78-82, Sep.-Oct. 2008.*
Jaini et al. An autoimmune-mediated strategy for prophylactic breast cancer vaccination. Nature Medicine. 16(7):799-803. published online May 30, 2010.*
Kesaraju et al. Development and characterization of murine experimental autoimmune mastitis. ProQuest Dissertations and Theses, Retrieved from http://search.proquest.com/docview/304763025?accountid=14753 (304763025) 2007.*
Richmond et al. Mouse xenograft models vs GEM models for human cacner therapeutics. Disease Models and Mechanisms. 1 (2-3):78-82, Sep.-Oct. 2008.*
Ragopathi. Antibody inducing polyvalent cancer vaccines. Cancer Treatment and Research. 123:157-180, 2005.*
Bowie et al. Deciphering the Message in Protein Sequences: Tolerance to Amino Acid Substitutions. Science, 247:1306-1310, 1990.*
Whisstock et al. Prediction of proteinfunction from protein sequence and structure. Quarterly Reviews in Biophysics. 36(3):307-340, 2007.*
Lazar et al. Transforming Growth Factor αx: Mutation of Aspartic Acid 47 and Leucine 48 Results in Different Biological Activities. Molecular and Cellular Biology. 1988; 8(3): 1247-1252.*
Hudis et al. "Triple_Negative Breast Cancer: An Unmet Medical Need" Oncologist, Jan. 1, 2011, vol. 16 Supp. 1, pp. 1-11.
Szabó TG, Palotai R, Antal P, Tokatly I, Tóthfalusi L, Lund O, Nagy G, Falus A, Buzás EI. Critical role of glycosylation in determining the length and structure of T cell epitopes. Immunome Res. 5, 4 (2009).
Finn OJ, Jerome KR, Henderson RA, Pecher G, Domenech N, Magarian-Blander J, Barratt-Boyes SM. MUC-1 epithelial tumor mucin-based immunity and cancer vaccines. Immunol. Rev. 145, 61-89 (1995).
Kimura T, Finn OJ. MUCI immunotherapy is here to stay. Expert Opin. Biol. Ther. 13, 35-49 (2013).
Giuffrida MG, Cavaletto M, Giunta C, Neuteboom B, Cantisani A, Napolitano L, Calderone V, Godovac-Zimmermann J, Conti A. The unusual amino acid triplet Asn-Ile-Cys is a glycosylation consensus site in human alpha-lactalbumin. J Protein Chem. 16, 747-53 (1997).
Picariello G, Ferranti P, Mamone G, Roepstorff P, Addeo F. Identification of N-linked glycoproteins in human milk by hydrophilic interaction liquid chromatography and mass spectrometry. Proteomics 8, 3833-47 (2008).

* cited by examiner

*Primary Examiner* — Vanessa L Ford
*Assistant Examiner* — Sandra Dillahunt
(74) *Attorney, Agent, or Firm* — Foley Hoag LLP

(57) ABSTRACT

Compositions and methods for immunization against human breast cancer are disclosed. A breast cancer vaccine comprises an immunogenic polypeptide comprising human α-lactalbumin.

10 Claims, 18 Drawing Sheets

ALPHA LACTALBUMIN IMMUNIZATION METHODS

CROSS REFERENCE TO RELATED APPLICATIONS

This application claims the benefit under 35 U.S.C. §119(e) of U.S. Provisional Application Ser. No. 61/353,464, filed Jun. 10, 2010, U.S. Provisional Application Ser. No. 61/353,470, filed Jun. 10, 2010, and U.S. Provisional Application Ser. No. 61/353,825, filed Jun. 11, 2010, the disclosures of each of which are hereby incorporated herein by reference in their entirety.

GOVERNMENT RIGHTS

This invention was made with government support under grant numbers RO1A1-51837, RO1DC-006422, and RO1CA14035 awarded by the National Institutes of Health. The U.S. Government has certain rights in the invention.

TECHNICAL FIELD

The present disclosure generally pertains to the fields of immunology and oncology. More particularly, the present disclosure pertains to the prevention or treatment of breast cancer by vaccination.

BACKGROUND AND SUMMARY

Breast cancer is responsible for the second overall cause of cancer-related deaths among women. Currently, prevention of breast cancer predominantly involves reducing modifiable risks including early detection through physical examination and mammograms, avoidance of unnecessary post-menopausal hormone therapy, reduction in alcohol consumption, loss of weight, increase in physical activity, and genetic testing for mutations of the breast cancer type 1 and type 2 susceptibility genes (BRCA1 and BRCA2, respectively). More aggressive approaches in high risk patients include chemoprevention with tamoxifen, raloxifene, and aromatase inhibitors as well as prophylactic bilateral mastectomy and oophorectomy.

Despite the profound health risk of breast cancer and inadequacy of preventative efforts, an immunotherapy for breast cancer has not been developed as an integral part of the standard of care. Tumor-specific antigens have long provided less than optimal results as targets for cancer vaccination. The overall goal of cancer vaccination has traditionally been to boost the latent immune response to tumor-specific antigens. Approaches have included cell-based protocols involving immunization with whole autologous or allogeneic tumors, as well as antigen-based strategies involving immunization with proteins or peptides overexpressed in tumors and underexpressed in normal tissues. The human epidermal growth factor receptor 2 (HER2) and mucin (MUC1) are the predominant antigens used in human breast cancer vaccine trials. Although vaccination using these antigens may demonstrate tumor reducing effects, neither antigen provides any tissue or tumor specificity since both are expressed in a variety of normal tissues and tumors. Thus, the lack of inherent tissue specificity of HER2 and MUC1 targeted immunity may ultimately lead to substantial systemic autoimmune sequelae if a robust immune response manifests.

A full-strength autoimmune attack sufficient to induce targeted breast failure can provide effective therapy against established breast malignancies if the target antigen is constitutively expressed in breast tumors. Moreover, if the selected target antigen is expressed in normal breast tissue under conditions that are easily avoidable, then the vaccine may provide safe and effective protection against the development of breast cancer.

Human alpha-lactalbumin ($\alpha$-lactalbumin) is a conditionally expressed, breast specific differentiation protein found in the majority of breast malignancies. As an integral differentiation protein involved in regulation of lactose biosynthesis, expression of $\alpha$-lactalbumin is breast-specific and conditionally dependent on lactation for its expression and synthesis. Human $\alpha$-lactalbumin is also constitutively overexpressed in the majority of breast tumors, is breast specific, and is sufficiently immunogenic to induce an effective proinflammatory immune response. Thus, immunization against human $\alpha$-lactalbumin offers a safe and effective vaccination strategy for the prevention of breast cancer.

BRIEF DESCRIPTION OF THE DRAWINGS

FIG. 3 shows that $\alpha$-lactalbumin vaccination prophylactically inhibits growth of breast tumors. The growth of autochthonous breast tumors is significantly inhibited in ten month old MMTV-neu mice immunized with $\alpha$-lactalbumin at eight weeks of age ($p=0.0004$.

FIG. 4 shows that $\alpha$-lactalbumin vaccination treats established growing transplanted breast tumors. Significant inhibition of 4T1 tumor growth occurs following $\alpha$-lactalbumin immunization at 5 days after tumor inoculation ($p<0.01$.

FIG. 7 shows that inhibition of tumor growth by α-lactalbumin vaccination is mediated by T cells. The transfer of α-lactalbumin primed LNC into naïve recipient BALB/c mice on the same day as inoculation with 4T1 tumors results in a) a significant inhibition of tumor growth (p<0.0001; FIG. 7A); b) a significant decrease in incidence of tumor bearing mice (p<0.03; FIG. 7B); and c) a significant decrease in final tumor weight (p<0.0008; FIG. 7C). Compared to ovalbumin (OVA) primed LNC, significant tumor growth inhibition occurs in naïve mice receiving either CD4+ T cells (p=0.002; FIG. 7D left panel) or CD8+ T cells (p=0.003; FIG. 7D right panel) that are enriched by magnetic bead separation from α-lactalbumin primed LNC. All error bars show ±SEM. Each * indicates a statistically significant difference.

Figure 8:
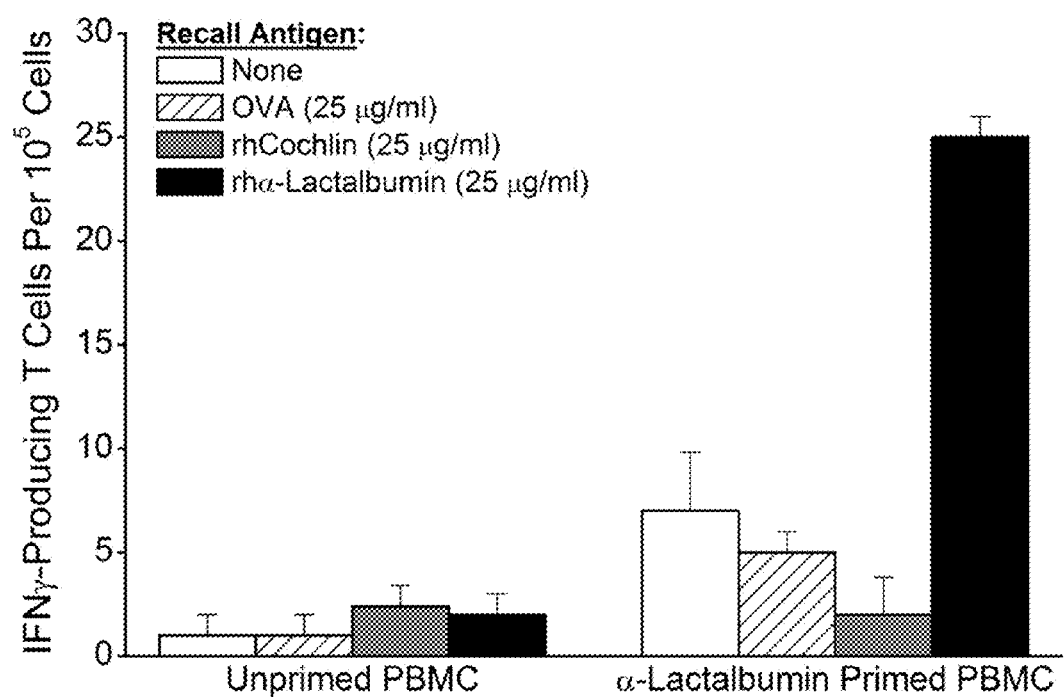

FIG. 8 shows in vitro priming of human peripheral blood mononuclear cells (PBMC) T cell using blood derived dendritic cells (DCs) to test for the availability of a human α-lactalbumin-reactive T cell repertoire. Priming of PMBCs with α-lactalbumin results in an increased frequency of IFNγ producing T cells upon subsequent presentation of α-lactalbumin (recall response).

DETAILED DESCRIPTION

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the scope of the invention.

In one embodiment, a human breast cancer vaccine comprising an immunogenic polypeptide is disclosed. The immunogenic polypeptide comprises human α-lactalbumin according to the amino acid sequence:

```
                                        (SEQ ID NO: 1)
kqftkcelsq llkdidgygg ialpelictm fhtsgydtqa ivennestey glfqisnklw ckssqvpqsr nicdiscdkf ldditddim cakkildikg idywlahkal ctekleqwlc ekl.
```

It is appreciated that human α-lactalbumin is processed in vivo by proteases to smaller peptide fragments, which are able to bind to MHC class I and/or MHC class II molecules on antigen presenting cells. Subsequently, T-cell receptors recognize and bind to the MHC molecule to which the peptide is bound, forming the primary signal that initiates an immune response.

In one embodiment, the vaccine further comprises an adjuvant and a pharmaceutically acceptable carrier. As used herein, the term "adjuvant" refers to an agent that stimulates the immune system and increases the response to a vaccine. Vaccine adjuvants are well-known to those of skill in the art. Illustratively, GPI-0100 is a suitable adjuvant for a vaccine. As used herein, the term "carrier" refers to an ingredient other than the active component(s) in a formulation. The choice of carrier will to a large extent depend on factors such as the particular mode of administration or application, the effect of the carrier on solubility and stability, and the nature of the dosage form. Pharmaceutically acceptable carriers for polypeptide antigens are well known in the art.

In one embodiment, the vaccine is administered prophylactically to prevent breast cancer. In one illustrative aspect, the vaccine is administered to non-lactating women at risk for developing breast cancer.

In one embodiment, the vaccine is administered to inhibit tumor cell expansion. The vaccine may be administered prior to or after the detection of breast tumor cells in a patient. Inhibition of tumor cell expansion is understood to refer to preventing, stopping, slowing the growth, or killing of tumor cells.

In one illustrative aspect, T cells of the human immune system are activated after administration of an immunogenic composition comprising human α-lactalbumin. The activated T cells may be CD4+ and/or CD8+.

In one embodiment, after administration of a vaccine comprising human α-lactalbumin, a proinflammatory response is induced by subsequent encounter of immune cells with α-lactalbumin. The proinflammatory immune response comprises production of proinflammatory cytokines and/or chemokines, for example, interferon gamma (IFNγ) and/or interleukin 2 (IL-2). Proinflammatory cytokines and chemokines are well known in the art.

It is to be appreciated that when the breast cancer vaccine is administered to patients whose breast tissue is not actively producing human α-lactalbumin in appreciable quantities (i.e. a non-lactating female, or a female devoid of α-lactalbumin producing breast tumor cells), immunization with human α-lactalbumin does not elicit a substantial inflammatory immune response (i.e. that is capable of causing breast tissue failure) in breast tissue. Subsequent encounter with human α-lactalbumin, such as that expressed by cells of a developing tumor elicits a recall response by the immune system. The recall response includes, but is not limited to, an increase in the production of proinflammatory cytokines such as IFNγ and IL-2, which promote a robust immune system attack against the α-lactalbumin expressing cells. In the instance in which human α-lactalbumin is produced only by cells of the human breast, the proinflammatory immune response will be breast tissue specific.

In one embodiment, a method of immunizing a human patient against human α-lactalbumin is disclosed. The method comprises the step of administering to the patient an immunogenic composition comprising a polypeptide comprising human α-lactalbumin (SEQ ID NO: 1). In one aspect, the immunogenic composition comprises a polypeptide that consists essentially of human α-lactalbumin.

In one embodiment, a method of activating human T cells capable of inducing a breast tissue specific inflammatory response in a human patient is disclosed. The method comprises the step of contacting the T cells with a composition comprising isolated human dendritic cells previously exposed to a polypeptide comprising human α-lactalbumin (SEQ ID NO: 1). The activated T cells exhibit a recall response when subsequently presented with human α-lactalbumin. The recall response includes the production of proinflammatory cytokines and or chemokines, including, for example, IFNγ.

In one embodiment, a vaccine for preventing or treating breast cancer is disclosed. The vaccine comprises an immunogenic polypeptide comprising human α-lactalbumin. After administration to patients that have breast tissue producing α-lactalbumin, the vaccine induces a breast tissue specific proinflammatory immune response.

In one embodiment, a method of treating cancer in a human patient is disclosed. The method comprises the step of administering to the patient a composition comprising human α-lactalbumin, an adjuvant, and a pharmaceutically acceptable carrier, in an amount effective to induce a breast tissue specific inflammatory response in the human patient. In one embodiment, the adjuvant is GPI-0100.

In one embodiment, a method of treating cancer in a human patient is disclosed. The method comprises the step of administering to the patient a composition, the composition comprising isolated human dendritic cells that have been loaded with human α-lactalbumin, in an amount effective to induce a breast tissue specific inflammatory response in the human patient.

In one embodiment, a method of inducing a breast tissue specific inflammatory response in a human patient is disclosed. The method comprises administering to the patient a composition, the composition comprising human α-lactalbumin, an adjuvant, and a pharmaceutically acceptable carrier, wherein an increase in α-lactalbumin reactive IFNγ producing T cells is produced after administration of the composition.

In one embodiment, a method of inducing a breast tissue specific inflammatory response in a human patient is disclosed. The method comprises administering to the patient a composition, the composition comprising isolated human dendritic cells that have been loaded with human α-lactabumin, wherein an increase in α-lactalbumin reactive IFNγ producing T cells is produced after administration of the composition.

An effective amount of human α-lactalbumin refers to an amount of human α-lactalbumin that is sufficient to be taken up by antigen presenting cells and/or activate T cells to elicit an immune response.

According to various embodiments for treatment or prevention of breast cancer, one or more booster injections of the vaccine are administered.

T cells recognize discrete peptides of protein antigens presented in the context of antigen presenting molecules that are typically expressed on macrophages and dendritic cells of the immune system. Peptide recognition typically occurs following phagocytic processing of the antigen by antigen-presenting cells and loading of small peptide fragments onto Major Histocompatibility Complex (MHC) class I and/or class II molecules. After CD4+ T cells recognize peptides presented on MHC class II molecules, they proliferate rapidly and become effector T cells that may activate other immune effector cells.

CD8+ T cells are believed to recognize peptides presented by MHC class I molecules, upon which they develop into cytotoxic effector cells capable of lysing and eliminating cells that express a particular protein. CD4 and CD8 molecules serve as co-receptors because their interactions with MHC molecules. They are believed to be required for an effective T cell mediated immune response.

The ability of human α-lactalbumin to be an effective polypeptide antigen in a vaccine against breast cancer depends on whether human α-lactalbumin is sufficiently immunogenic in humans to generate a proinflammatory immune response. The immunogenicity of a particular protein, such as human α-lactalbumin, is highly unpredictable, and depends in part upon the particular amino acid sequence of the protein, its uptake and processing by antigen presenting cells into smaller peptide fragments, the availability of appropriate MHC binding sites for the processed peptide fragments, and the availability of appropriately responsive T cells with specific receptor sequences that can recognize and bind the peptide in the context of the MHC binding pocket.

EXAMPLES

Example 1

α-Lactalbumin Immunization Activates both CD4+ and CD8+ Proinflammatory T Cells

Figure 1A:
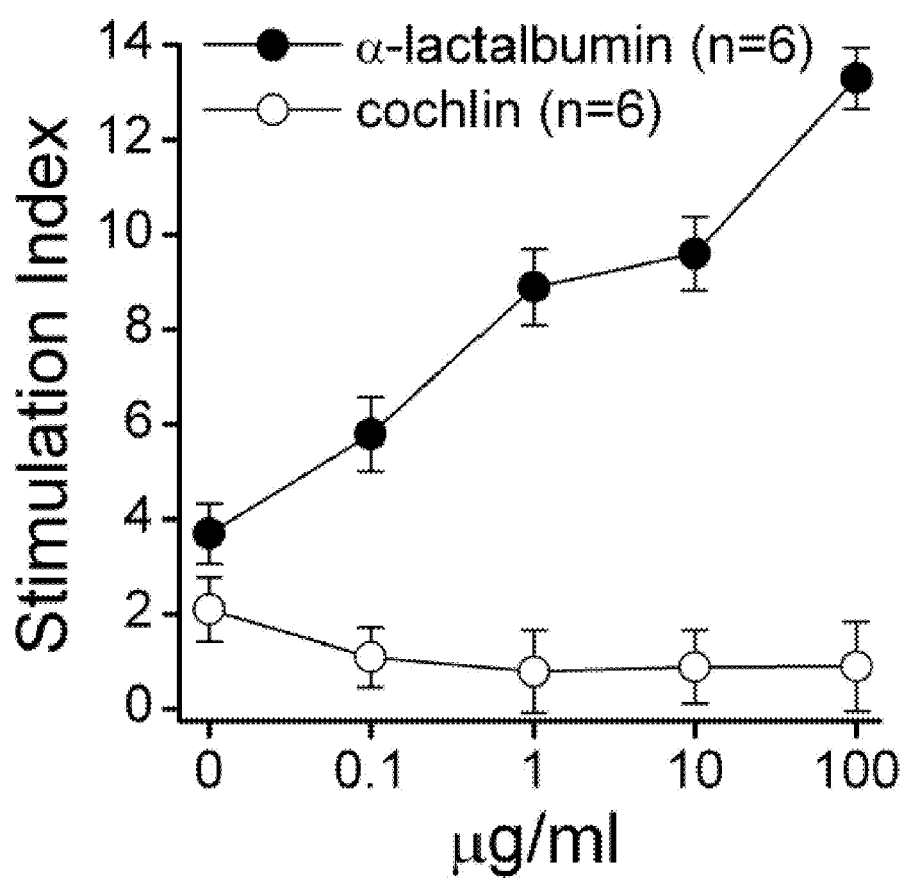
FIG. 1 shows the immunogenicity of recombinant mouse $\alpha$-lactalbumin. Lymph node cells are evaluated 10 days after immunization of SWXJ female mice with $\alpha$-lactalbumin and show recall responses that are a) antigen-specific to recombinant mouse $\alpha$-lactalbumin but not to recombinant human cochlin over a dose range (see FIG. 1A); b) elicited from both purified $CD4^+$ and $CD8^+$ T cells in response to 25 pg/ml $\alpha$-lactalbumin (see FIG. 1B); and c) consistent with a proinflammatory type 1 cytokine profile with high production of IFN$\gamma$ and IL-2 and low production of the type 2 cytokines, IL-4, IL-5, and lactalbumin. All error bars show ±SEM.
Figure 1B:
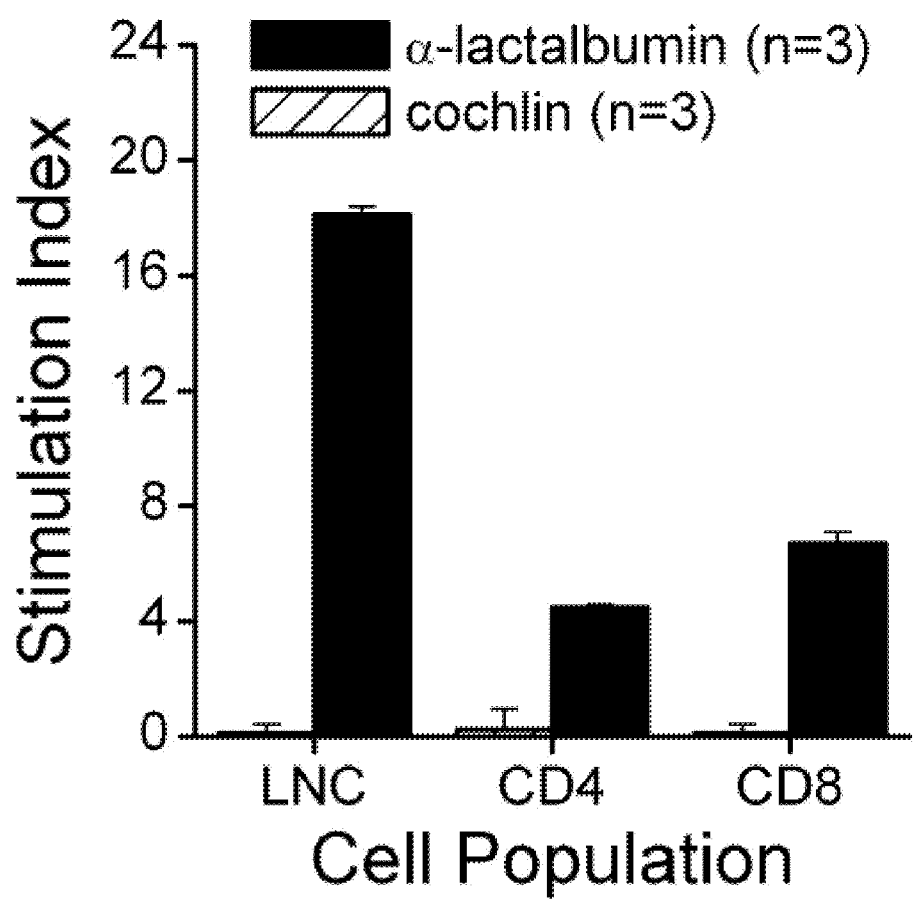
Figure 1C:
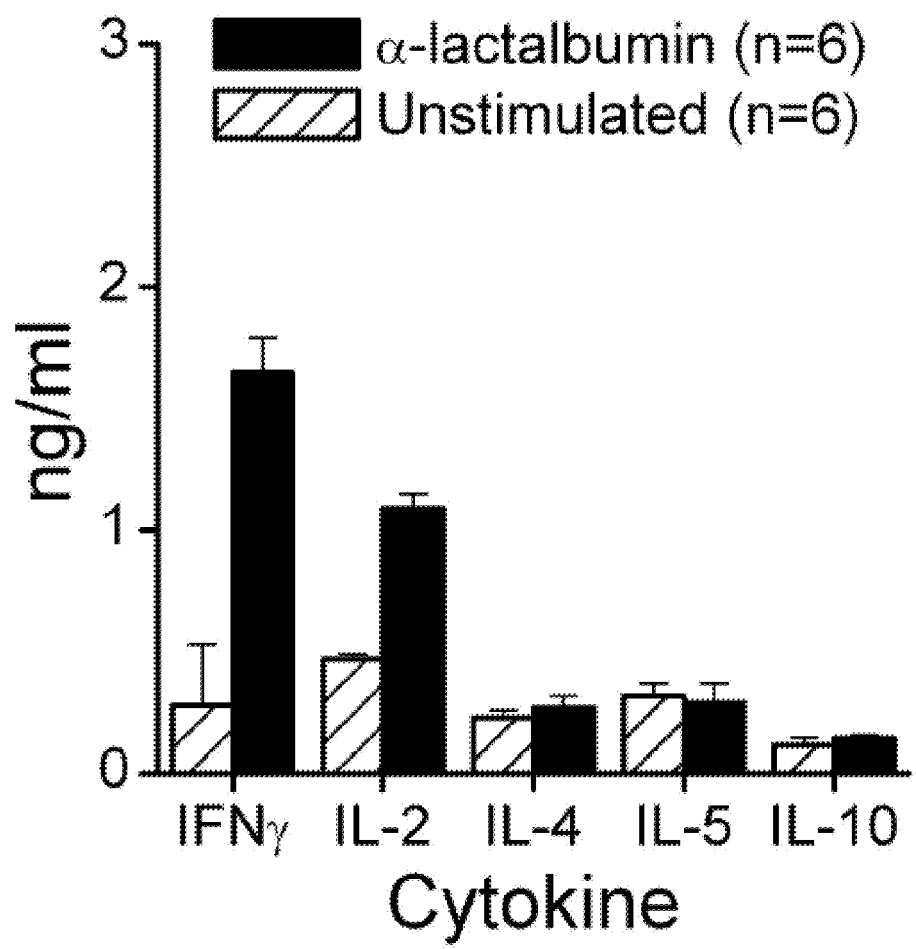

Recombinant mouse α-lactalbumin is purified under denaturing conditions using nickel-nitrilotriacetic acid affinity chromatography followed by reverse phase HPLC. Female SWXJ mice are immunized with recombinant mouse α-lactalbumin. Ten days after immunization, lymph node cells (LNC) in the mice show a dose-dependent proliferation in recall responses to α-lactalbumin and are unresponsive to recombinant human cochlin generated in $E.\ coli$ in a virtually identical manner (see FIG. 1A). Both CD4+ and CD8+ T cells are involved in responsiveness to α-lactalbumin (see FIG. 1B). Furthermore, α-lactalbumin shows a proinflammatory phenotype involving a high production of interferon-gamma (IFNγ) and IL-2 and a low production of IL-4, IL-5, and IL-10 (see FIG. 1C).

Example 2

Figure 2:
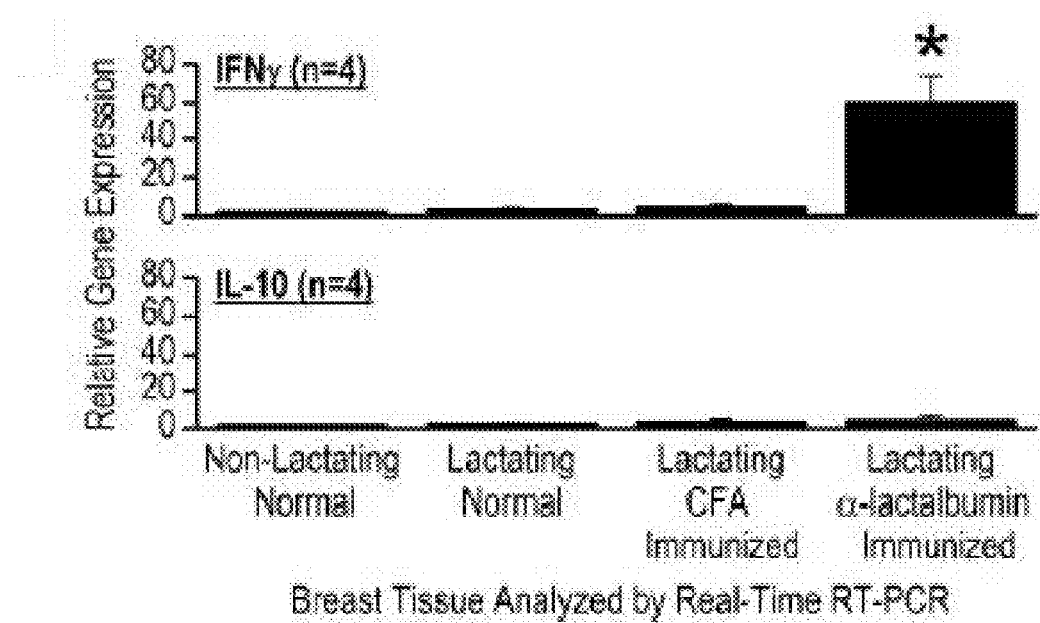
FIG. 2 shows the analysis of breast tissue during autoimmune-induced breast failure. Real-time RT-PCR analysis of lactating mammary tissue shows significantly elevated expression levels of IFN$\gamma$ ($p=0.001$) but not IL-10 ($p>0.10$). All error bars show ±SEM. Each * indicates a statistically significant difference.

Immunization of Non-Lactating Mice with α-Lactalbumin Fails to Induce Breast Inflammation Breast tissue from non-lactating mice immunized with α-lactalbumin does not demonstrate inflammatory infiltration, but instead consistently shows isolated individual CD3+ T cells migrating through breast parenchyma. However, extensive T cell infiltrates consistently occur throughout the mammary tissue of lactating mice immunized with α-lactalbumin. Breast tissue from lactating control mice immunized with CFA alone does not show inflammatory T cell infiltration. Analysis of breast infiltrating T cells by flow cytometry shows a high frequency of CD3+CD4+ T cells and CD3+CD8+ T cells expressing the $CD44^{high}$ activation marker. Analysis by quantitative real-time RT-PCR shows that breast tissue from lactating mice immunized with α-lactalbumin have significantly elevated expression levels of IFNγ ($p=0.001$) but not IL-10 ($p>0.10$) compared to levels expressed in breast tissue from untreated normal non-lactating or lactating mice, or from lactating mice immunized with CFA alone (see FIG. 2).

Example 3

Prophylactic α-Lactalbumin Vaccination Inhibits Growth of Breast Tumors

Figure 3A:
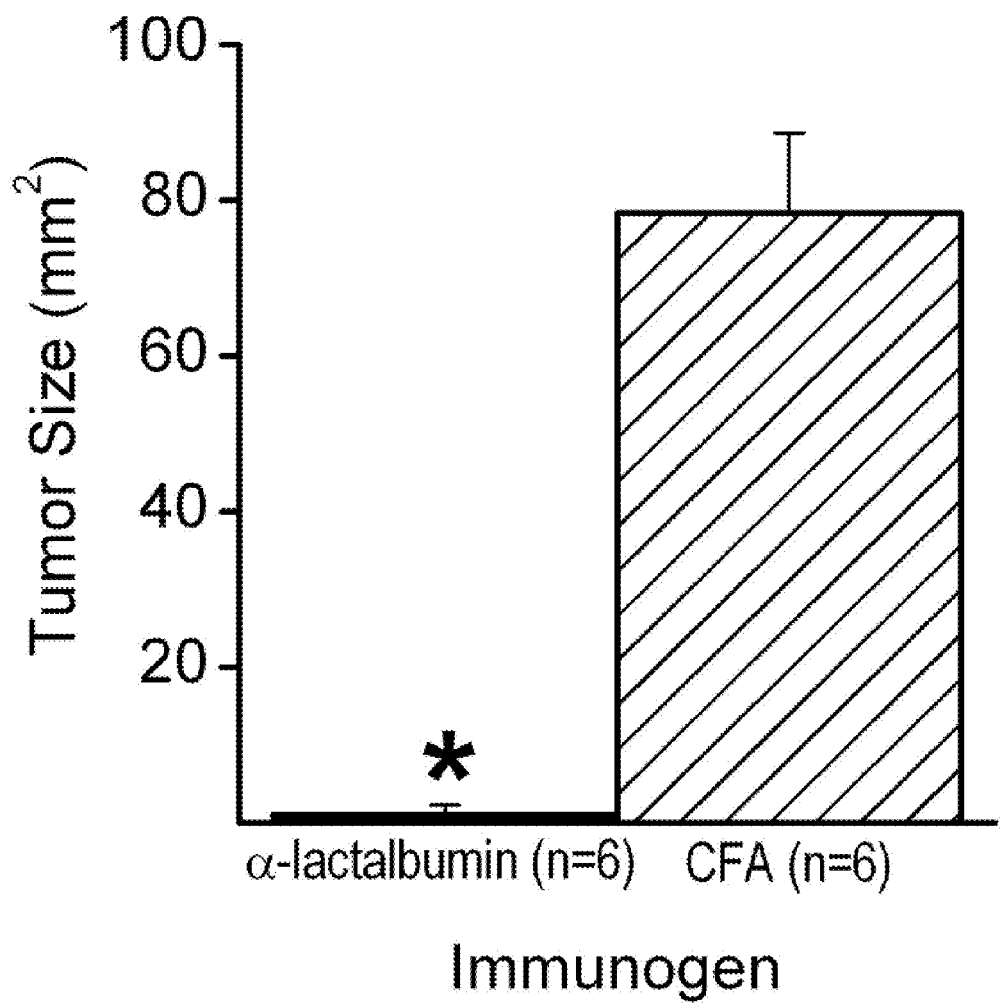
FIG. 3A). Growth of transplanted 4T1 tumors is significantly inhibited following prophylactic immunization with $\alpha$-lactalbumin 13 days prior to tumor inoculation ($p=0.0006$.

MMTV-neu mice express the unactivated neu (ErbB2 or HER2/neu) protooncogene under the regulation of the long terminal repeat of mouse mammary tumor virus (MMTV) and show a 50% incidence of spontaneous mammary tumors by 205 days of age. Eight week old MMTV-neu mice are immunized with either α-lactalbumin in CFA or with CFA alone. All mice are euthanized when the first tumor reached 17 mm in diameter (at around 10 months of age). Upon completion of the experiment, all CFA-immunized control mice develop breast tumors upon. In comparison, none of the mice immunized with α-lactalbumin show any detectable mammary tumors ($p=0.0004$; see FIG. 3A).

Figure 3B:
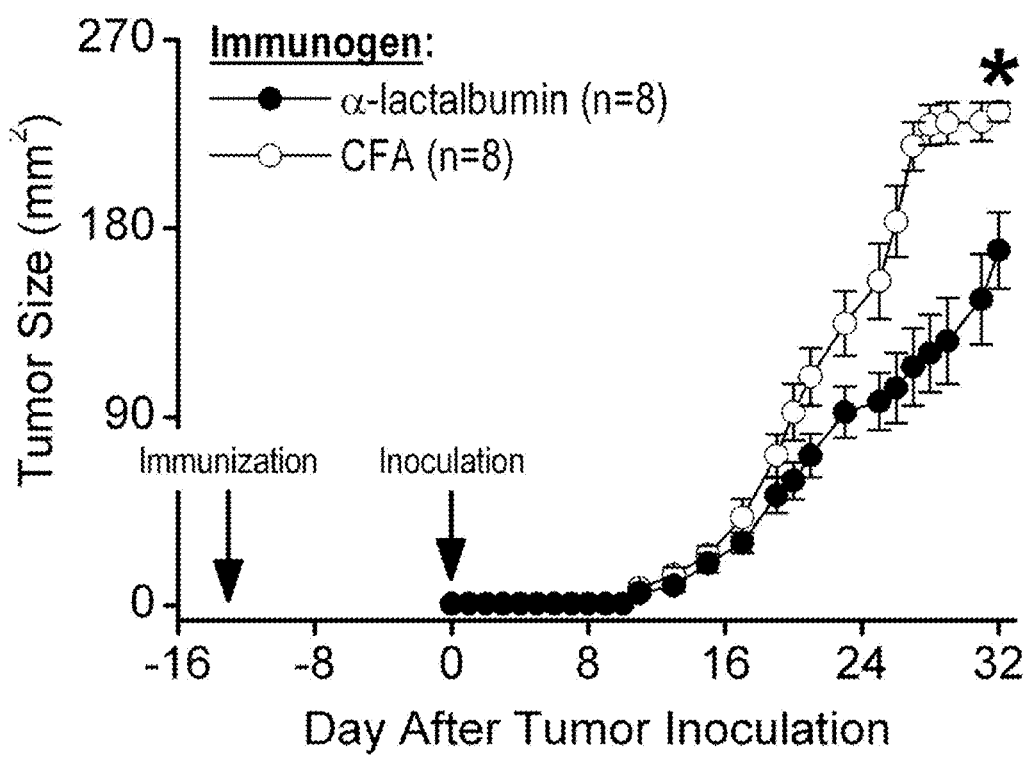
FIG. 3B). All error bars show ±SEM. Each * indicates a statistically significant difference.

Prophylactic vaccination with α-lactalbumin is also effective against transplantable 4T1 tumors. BALB/c mice immunized with α-lactalbumin 13 days prior to inoculation with 4T1 tumor cells exhibit significant growth inhibition ($p=0.0006$; see FIG. 3B).

Figure 4A:
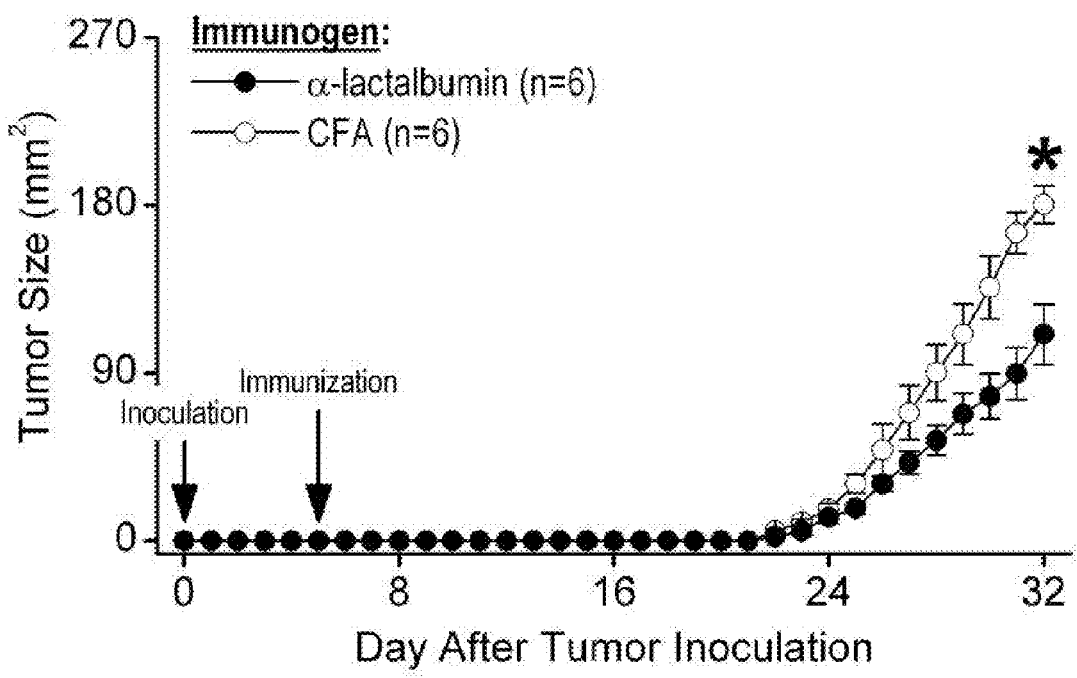
FIG. 4A) and at 13 days after tumor inoculation ($p<0.01$.
Figure 4B:
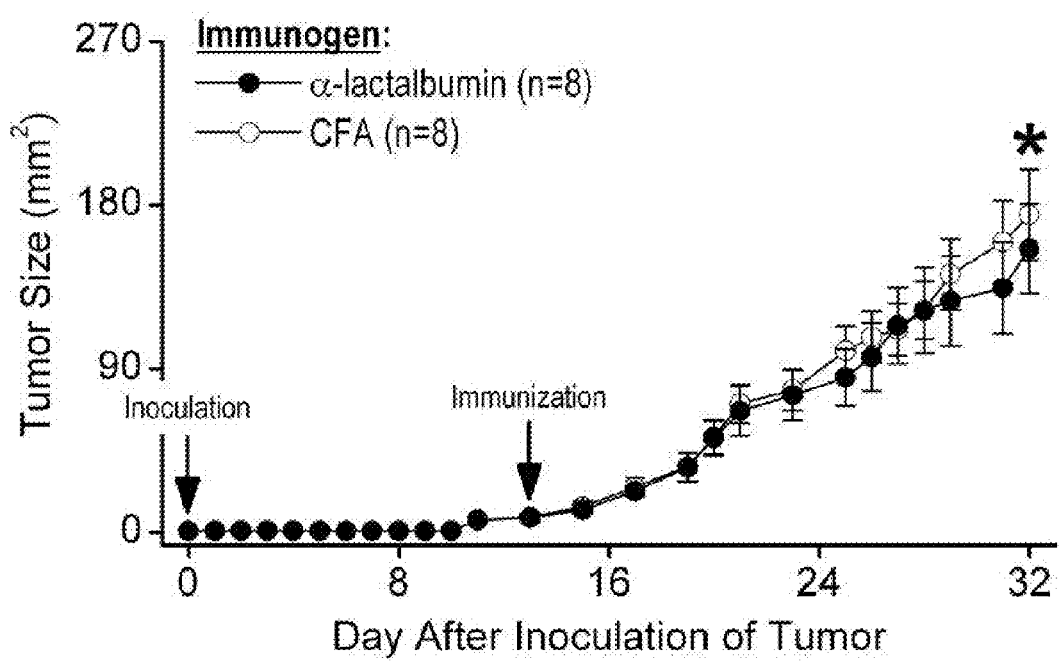
FIG. 4B), but not at 21 days after tumor inoculation ($p>0.10$.
Figure 4C:
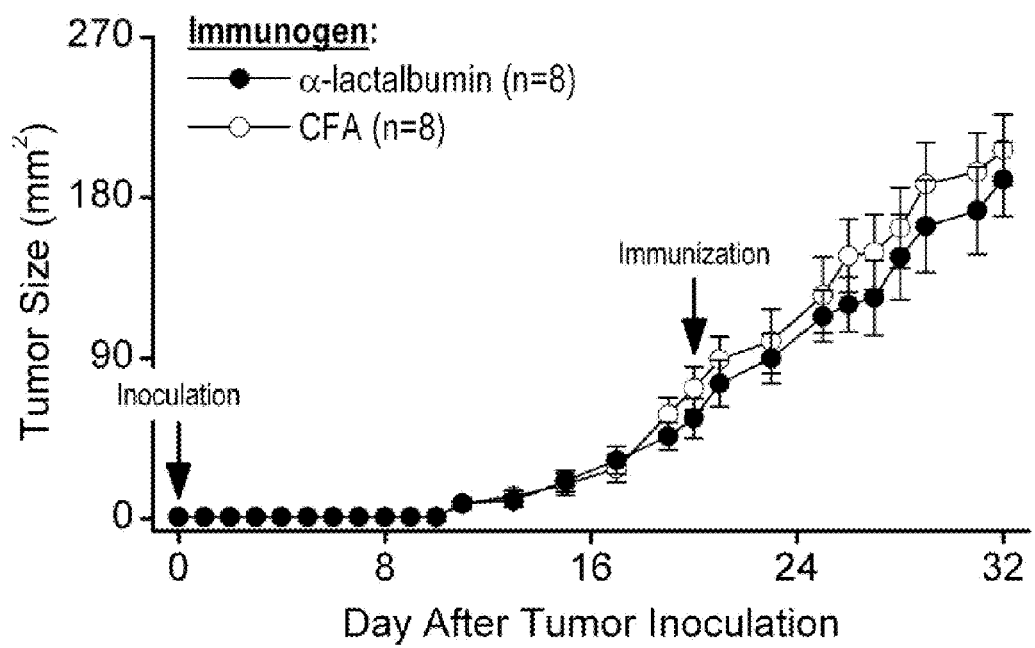
FIG. 4C). All error bars show ±SEM. Each * indicates a statistically significant difference.

Example 4

α-Lactalbumin Vaccination Inhibits Growth of Established Transplanted 4T1 Breast Tumors Following subcutaneous inoculation of BALB/c mice with $2 \times 10^4$ 4T1 tumor cells, tumors are well established within 5 days after inoculation and palpable tumors are present within 2 to 3 weeks after inoculation. After inoculation with 4T1 tumor cells, vaccination with α-lactalbumin is performed at 5 days after inoculation, at 13 days after inoculation, and at 21 days after inoculation. A significant inhibition of tumor growth is observed at the 5-day vaccination (p<0.01; see FIG. 4A) and at the 13-day vaccination (p<0.01; see FIG. 4B) but not at the 21-day vaccination (see FIG. 4C). The lack of tumor growth inhibition in mice vaccinated 21 days after inoculation may be due to the shortened 11-day observation period between the time of immunization and the time when tumors reach the maximum size mandating euthanasia.

Figure 5:
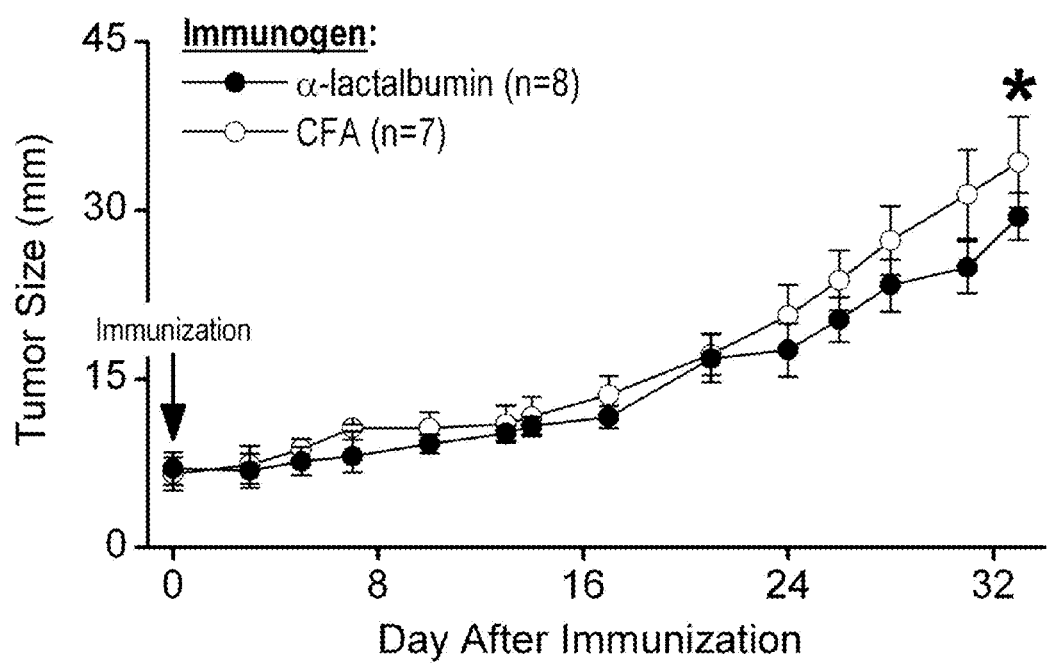
FIG. 5 shows that $\alpha$-lactalbumin vaccination treats established growing autochthonous breast tumors. Significant inhibition ($p<0.0006$) in the growth of extremely aggressive autochthonous tumors occurs following $\alpha$-lactalbumin immunization of MMTV-PyVT transgenic mice at 6 weeks of age. Due to massive multifocal tumor growth, tumors in MMTV-PyVT mice are amenable to measurement in only one direction. The longest measurements on all ten MMTV-PyVT tumors are added to calculate total tumor load in mm on each day.

Example 5

α-Lactalbumin Vaccination Inhibits Growth of Established Autochthonous Breast Tumors MMTV-PyVT transgenic mice demonstrate loss of lactational ability coincident with transgene expression and develop palpable very aggressively growing mammary tumors by 5 weeks of age. In this example, MMTV-PyVT transgenic mice are vaccinated at 6 weeks of age with α-lactalbumin. Significant inhibition in the growth of very aggressive established autochthonous tumors in MMTV-PyVT is observed (p<0.0006; see FIG. 5). Thus, α-lactalbumin vaccination indicates effective protection and therapy against breast tumor growth and is particularly effective when immunization occurs prior to the appearance of palpable tumors in MMTV-PyVT transgenic mice.

Example 6

α-Lactalbumin-Specific T Cells Induce Tumor Inflammation and Cytotoxicity

BALB/c mice are vaccinated with α-lactalbumin and inoculated with 4T1 cells. Approximately 32 days after inoculation, tumors in the BALB/c mice show extensive infiltration of $CD3^+$ T cells. In comparison, these inflammatory infiltrates do not occur in tumors from control mice immunized with CFA. How cytometry analysis of tumor infiltrating lymphocytes (TILs) show a predominance of $CD4^+$ (64.3%) T cells compared to $CD8^+$ (14.4%) T cells.

Figure 6A:
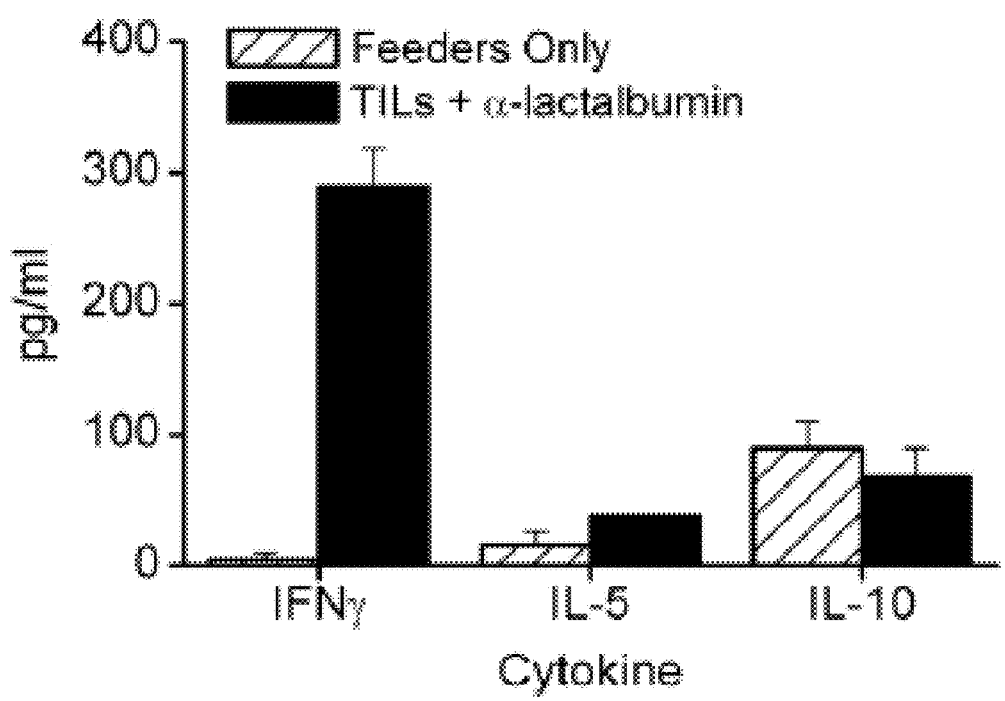
FIG. 6 shows that $\alpha$-lactalbumin-specific T cells induce tumor inflammation and cytotoxicity. Recall responses to $\alpha$-lactalbumin as measured by ELISA demonstrate a type-1 proinflammatory phenotype involving high production of IFNγ compared to IL-5 and IL-10 (FIG. 6A). ELISPOT analysis of TILs shows that CD4+ rather than CD8+ T cells produce IFNγ (FIG. 6B). Death of cultured 4T1 tumor cells is inhibited by treatment of cultured α-lactalbumin primed LNC with antibodies specific for mouse CD8, indicating that CD8+ T cells mediate 4T1 specific cytotoxicity (FIG. 6C).
Figure 6B:
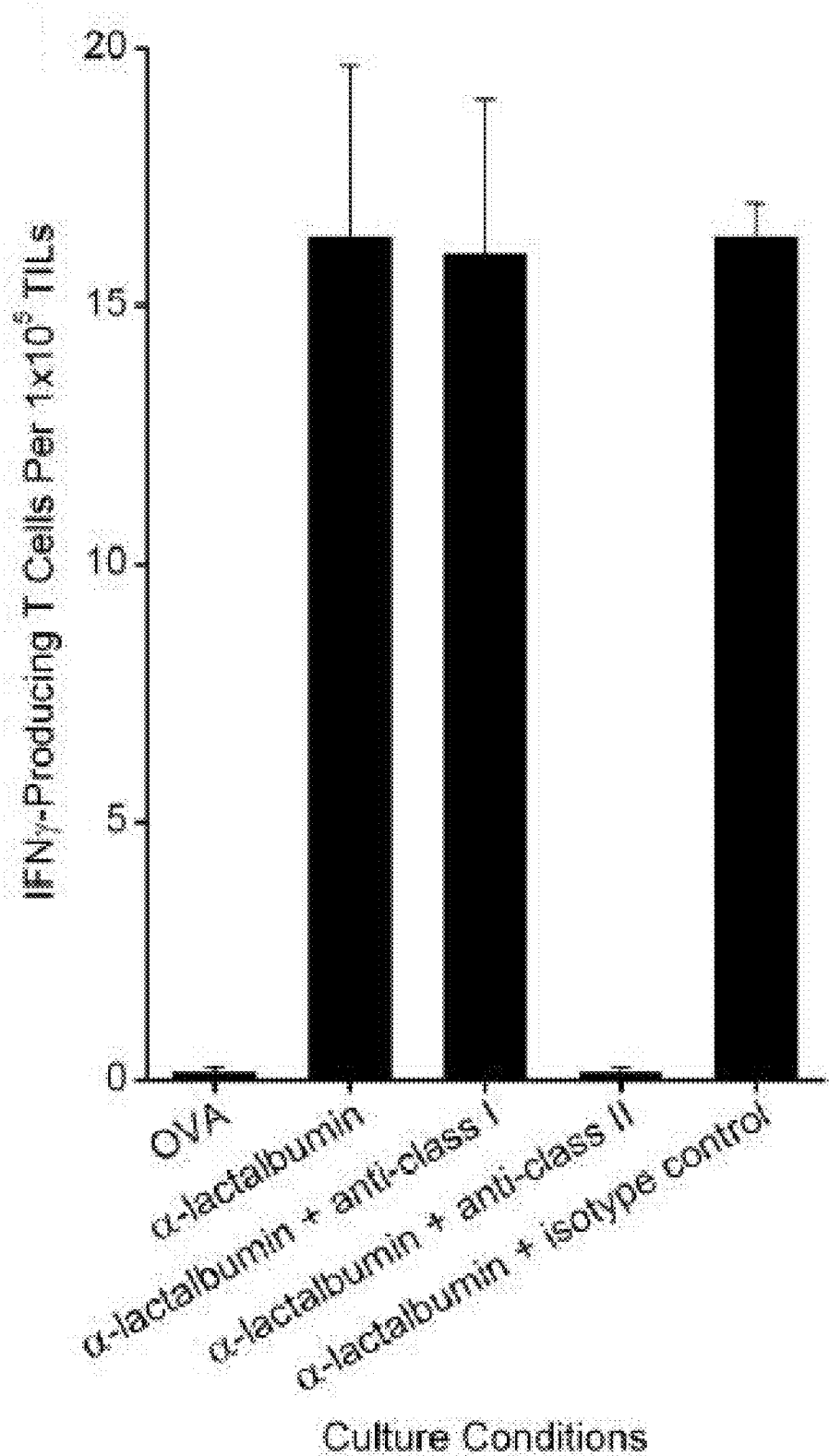
Figure 6C:
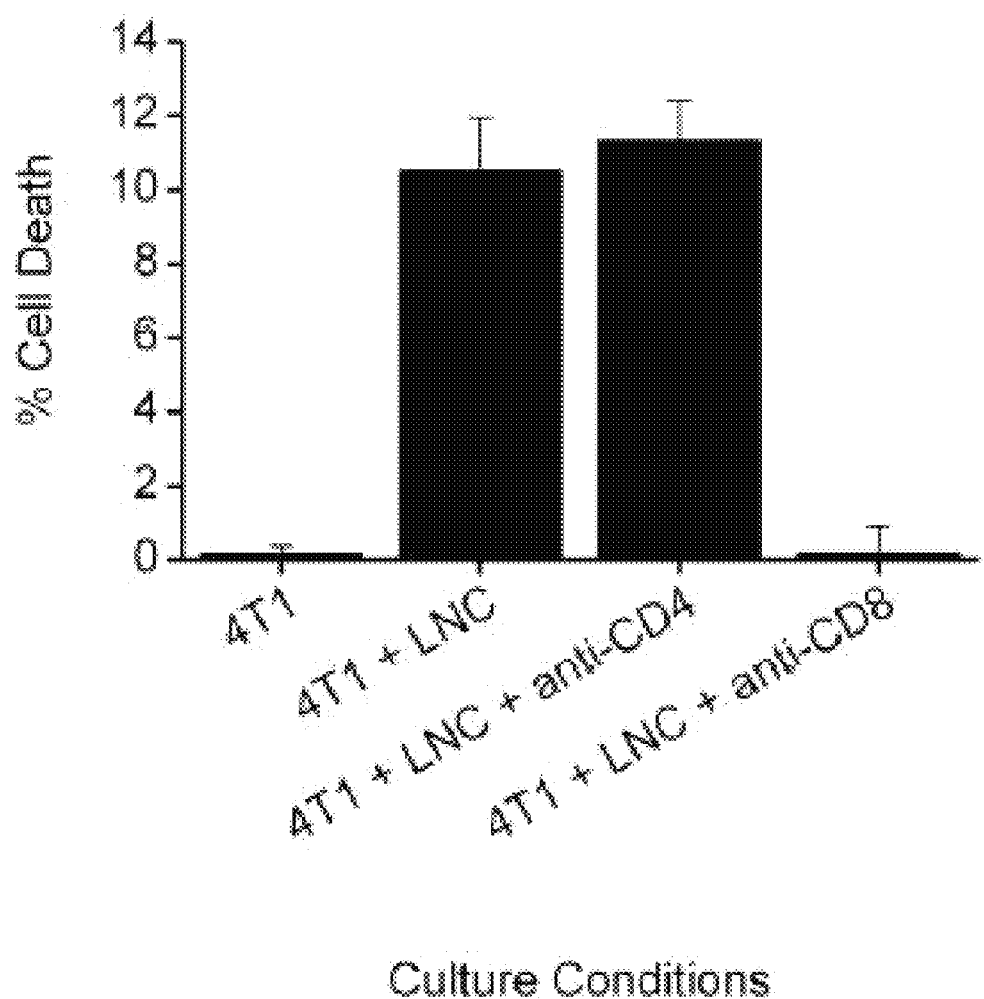
Figure 7A:
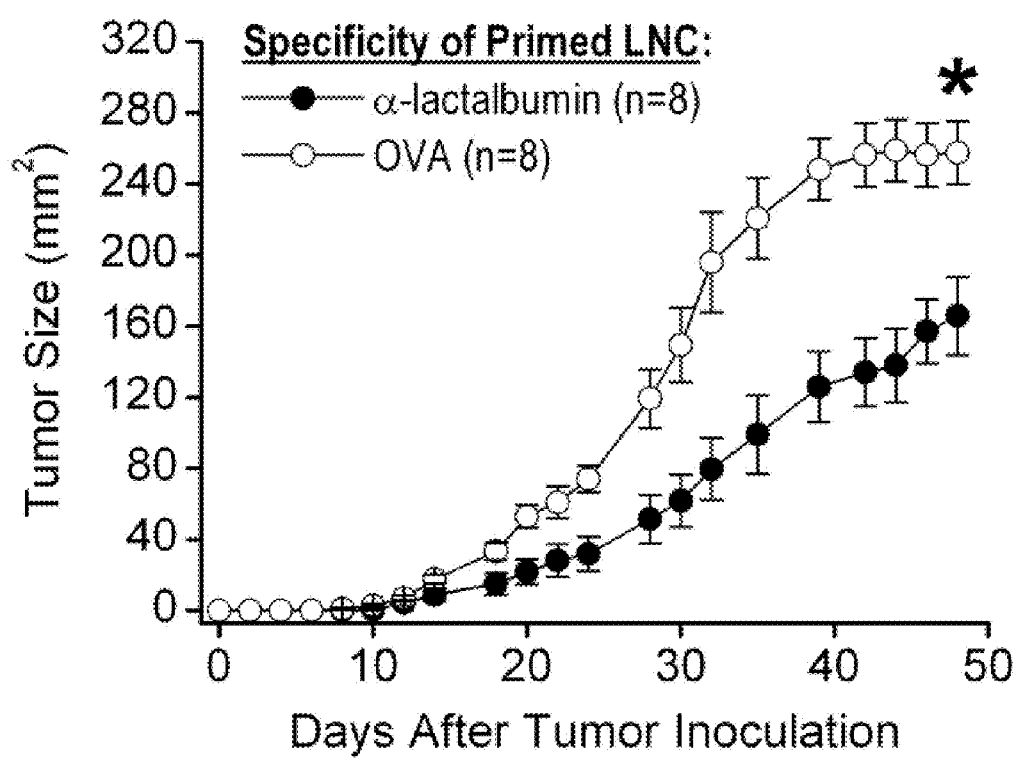
Figure 7B:
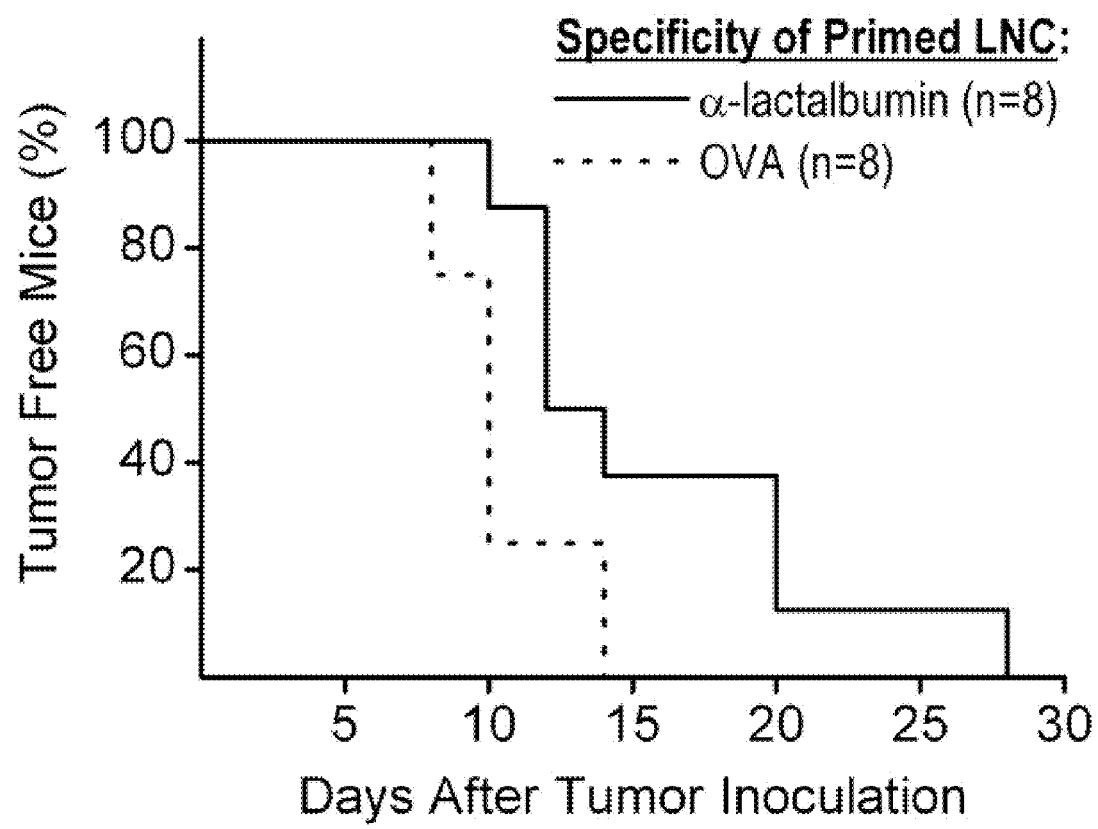
Figure 7C:
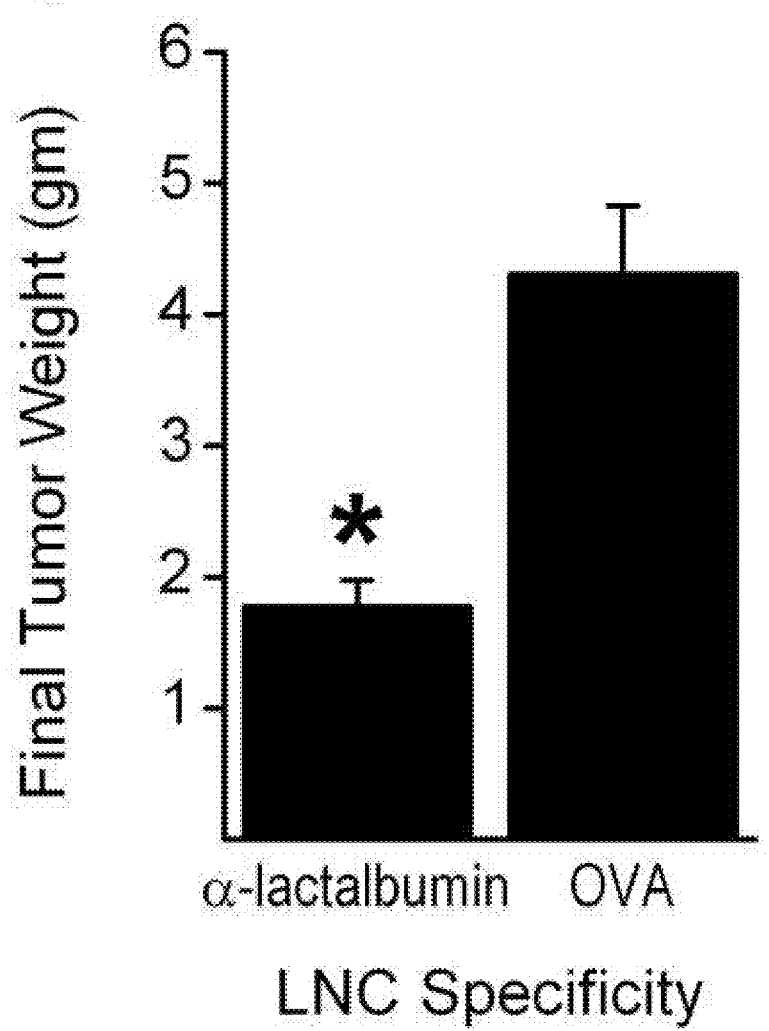
Figure 7D:
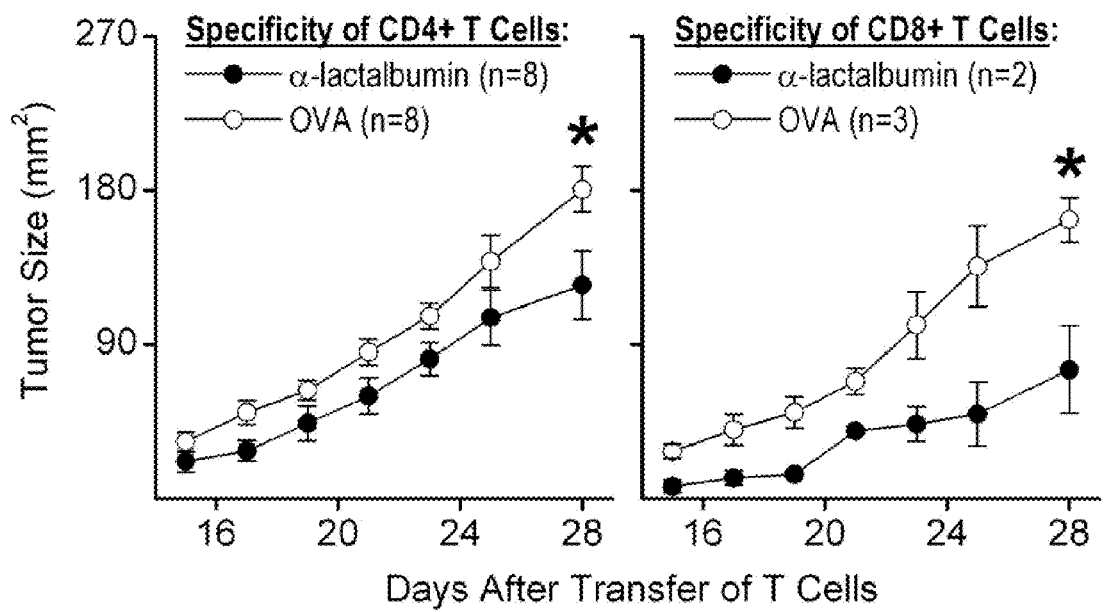

Furthermore, recall responses to 50 μg/ml α-lactalbumin as measured by ELISA demonstrate a type-1 proinflammatory phenotype involving high production of IFNγ compared to IL-5 and IL-10 (see FIG. 6A). ELISPOT analysis of TILs shows that $CD4^+$ rather than $CD8^+$ T cells are produced the IFNγ since its secretion by cultured T cells is inhibited by treatment with class II but not class I specific antibodies (see FIG. 6B). However, death of cultured 4T1 tumor cells is inhibited by treatment of cultured α-lactalbumin primed LNC with antibodies specific for mouse CD8 but not CD4 (see FIG. 6C). This result indicates that $CD8^+$ T cells mediate 4T1 specific cytotoxicity.

Example 7

Inhibition of Breast Tumor Growth by α-Lactalbumin Vaccination is Mediated by T Cells On the same day, naïve recipient BALB/c mice are inoculated with 4T1 tumors and α-lactalbumin-primed LNC. A significant inhibition of tumor growth is observed in these mice (p<0.0001; see FIG. 7A). Furthermore, the incidence of tumor bearing mice is significantly decreased in this example (p<0.03; see FIG. 7B) and the final tumor weight is also significantly decreased (p<0.0008; see FIG. 7C).

Naïve mice further received a) $CD4^+$ T cells enriched by magnetic bead separation from α-lactalbumin-primed LNC, b) $CD8^+$ T cells enriched by magnetic bead separation from α-lactalbumin-primed LNC, or c) control ovalbumin (OVA)-primed LNC. Significant tumor growth inhibition is observed in the mice receiving the $CD4^+$ T cells enriched by magnetic bead separation from α-lactalbumin-primed LNC (p=0.002; see FIG. 7D, left panel) and the $CD8^+$ T cells enriched by magnetic bead separation from α-lactalbumin-primed LNC (p=0.003; see FIG. 7D, right panel) compared to OVA-primed LNC. This example indicates that activated $CD4^+$ and $CD8^+$ TILs mediate the protective and therapeutic effects of α-lactalbumin vaccination on breast tumor growth.

Example 8

Availability of α-Lactalbumin Responsive T Cells in Females

T cell repertoire availability and magnitude is assessed in peripheral blood mononuclear cells (PBMC) by in vitro priming against α-lactalbumin and measurement of the resulting antigen-specific frequencies of IFNγ-producing T cells. Monocyte derived DCs were prepared from PBMC taken from a 29 year-old female patient. Adherent cell selection was followed by culture in X-VIVO media (BioWhittaker, Walkersville, Md.) with 500 U/ml rhGMCSF and rhIL-4 (Pepro-tech, Rocky Hill, N.J.). Six days after initiation of culture, DCs were pulsed with 75 μg/ml of purified recombinant human α-lactalbumin (rhα-lactalbumin) and were washed extensively 48 hours later. The washed DCs were co-cultured with nylon wool purified naive T cells from the same donor at a ratio of 1:5 (DCs to T cells). Approximately 72 hours after co-culture, in vitro primed T cells and unprimed T cells from the same donor were enriched by passage through nylon wool and re-cultured with γ-irradiated (3000 rads) PBMC as feeder cells at a ratio of 1:10 (feeders to T cells) on ELISPOT plates (Polyfiltronics, Rockland, Mass.) pre-coated with mouse anti-human IFNγ capture antibody (#M-700A; Endogen, Cambridge, Mass.). Frequencies of α-lactalbumin reactive IFNγ producing T cells were determined 48 hours later using secondary biotinylated mouse anti-human IFNγ (#M701; Endogen) and resolution of ELISPOTS using an automated Immunospot Satellite Analyzer (Cellular Technology, Cleveland, Ohio).

After priming with α-lactalbumin, the PMBCs demonstrate an increased frequency of IFNγ producing T cells (see FIG. 8) upon subsequent exposure to α-lactalbumin (recall response). The observed response is antigen specific, as recall antigens OVA and recombinant human cochlin (rmCochlin), an inner ear protein generated in transduced E. coli in a manner similar to the production of recombinant human α-lactalbumin, do not elicit an increase in IFNγ producing T cells.

Taken together, the results described herein show that show that 1) immunization with α-lactalbumin activates both $CD4^+$ and $CD8^+$ proinflammatory T cells; 2) immunization of non-lactating mammals with α-lactalbumin fails to induce breast inflammation; 3) prophylactic α-lactalbumin vaccination inhibits growth and incidence of breast tumors; and 4) α-lactalbumin vaccination inhibits growth of established tumors. α-lactalbumin immunization provides a safe and effective vaccination in several murine breast cancer models.

Importantly, it is also demonstrated herein that human α-lactalbumin is sufficiently immunogenic in humans to activate T cells and elicit a proinflammatory immune recall response. Thus, immunization of humans with human α-lactalbumin has the ability to provide a safe and effective vaccine for human breast cancer.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present invention.

What is claimed is:

1. A method of immunizing a non-lactating female human patient against a human α-lactalbumin, the method comprising the step of inducing an immune response against α-lactalbumin in said patient by administering to the patient an immunogenic composition, said composition comprising an adjuvant; and a purified recombinant polypeptide consisting of a human α-lactalbumin sequence as set forth in SEQ ID NO: 1.

2. The method of claim 1, wherein T cells are activated after administration of the polypeptide to the patient.

3. The method of claim 2, wherein the T cells are CD4+.

4. The method of claim 2, wherein the T cells are CD8+.

5. The method of claim 1, wherein a proinflammatory immune response is induced by subsequent encounter of immune cells with α-lactalbumin.

6. The method of claim 5, wherein the proinflammatory immune response comprises production of IFNγ by T cells.

7. The method of claim 5, wherein the proinflammatory immune response is breast tissue specific.

8. The method of claim 1, wherein said patient has a breast tumor that overexpresses α-lactalbumin.

9. The method of claim 1, wherein the adjuvant is GPI-0100.

10. The method of claim 1, wherein the recombinant polypeptide is produced in *Escherichia coli*.

* * * * *

SEQUENCE LISTING

<160> NUMBER OF SEQ ID NOS: 1

<210> SEQ ID NO 1
<211> LENGTH: 123
<212> TYPE: PRT
<213> ORGANISM: Homo sapiens

<400> SEQUENCE: 1

Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Cys Lys Ser Ser
    50                  55                  60

Gln Val Pro Gln Ser Arg Asn Ile Cys Asp Ile Ser Cys Asp Lys Phe
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120